United States Patent
Lancesseur et al.

(10) Patent No.: US 6,187,269 B1
(45) Date of Patent: *Feb. 13, 2001

(54) ASSAY DEVICES

(75) Inventors: Didier Lancesseur, Choisy-le-Roi (FR); Stewart John Wiles, Rushden (GB)

(73) Assignee: Unipath Limited, Hampshire (GB)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/616,566

(22) Filed: Mar. 15, 1996

(30) Foreign Application Priority Data

Mar. 17, 1995 (GB) ................................... 9505425

(51) Int. Cl.[7] ................................... G01N 33/48
(52) U.S. Cl. ................................ 422/61; 422/58; 436/165; 436/169
(58) Field of Search ................. 422/56, 58, 61; 436/165, 169

(56) References Cited

U.S. PATENT DOCUMENTS

| | | | |
|---|---|---|---|
| 4,977,009 | * 12/1990 | Anderson et al. | 429/76 |
| 5,432,214 | 7/1995 | Lancesseur | 524/12 |
| 5,460,777 | * 10/1995 | Kitajima et al. | 422/58 |
| 5,504,013 | * 4/1996 | Senior | 436/165 |
| 5,602,037 | * 2/1997 | Ostgaard et al. | 422/58 |
| 5,622,871 | * 4/1997 | May et al. | 422/58 |

FOREIGN PATENT DOCUMENTS

| | | |
|---|---|---|
| 0 454 967 A2 | 11/1981 | (EP) . |
| 0 253 579 | 1/1988 | (EP) . |
| 0 260 965 | 3/1988 | (EP) . |
| 0 291 194 | 11/1988 | (EP) . |
| 2 029 363 | 3/1980 | (GB) . |
| WO 96/04189 | 2/1996 | (WO) . |

* cited by examiner

Primary Examiner—Lyle A. Alexander
(74) Attorney, Agent, or Firm—Pillsbury Madison & Sutro LLP

(57) ABSTRACT

Storage stability of an assay device, comprising an assay strip and sensitive reagents such as antibodies within a plastics casing, is maintained by moulding some or all of the casing from dessicant-containing plastics material, especially a blend of about 60–65% polystyrene and about 30% silica dust. Ideally the desiccant-containing plastics material is used in the moulding of a removable cap for the device. The cap can be made by sandwich injection moulding, using the dessicant-containing polystyrene as a core, surrounded by conventional polystyrene.

5 Claims, 2 Drawing Sheets

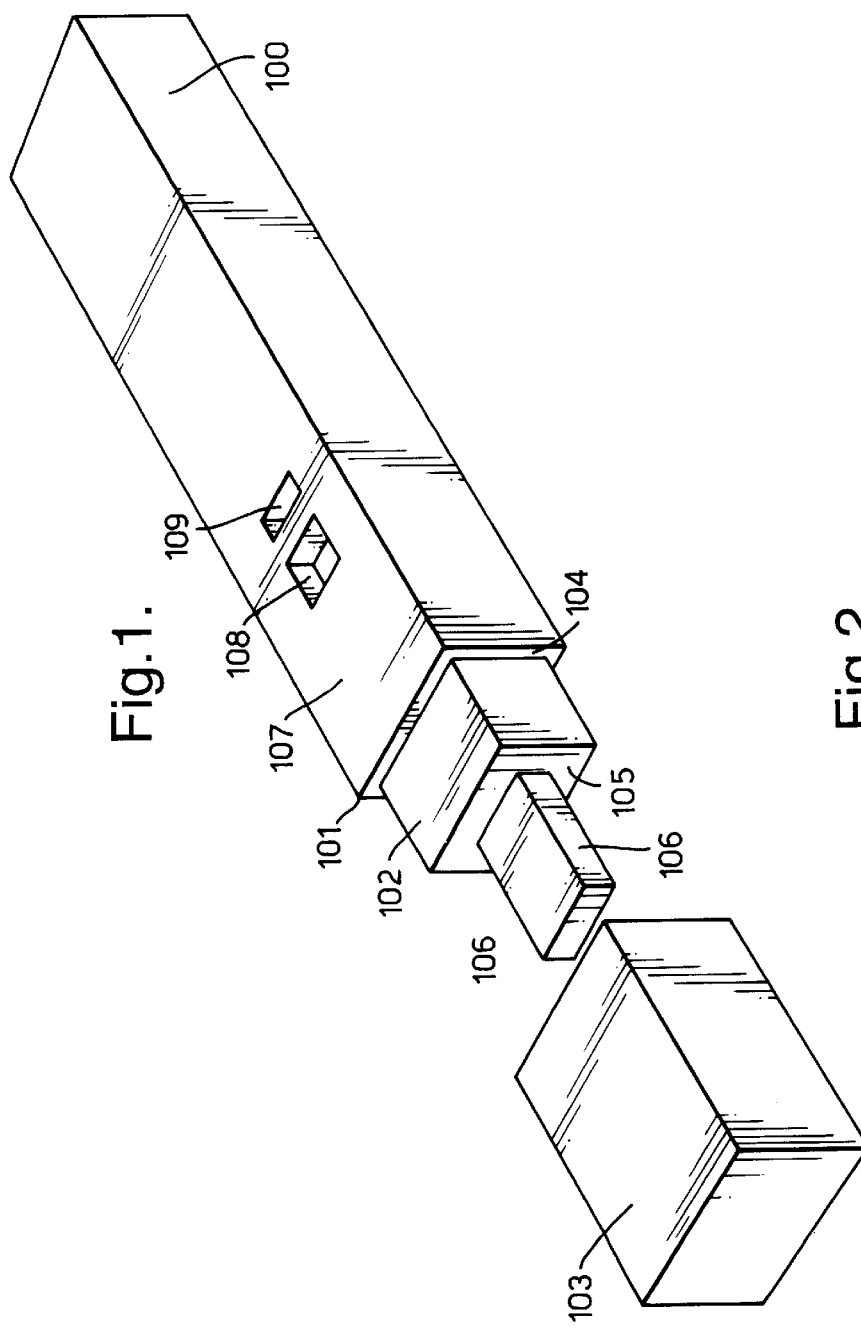

ASSAY DEVICES

FIELD OF THE INVENTION

This invention relates to assay devices. More particularly it relates to ways in which sensitive reagents within such devices may be protected against moisture-induced degradation during storage.

BACKGROUND TO THE INVENTION

Many assay devices are now available commercially which are intended for quick simple tests in professional circumstances (clinics and doctor's offices) or in the home (for example pregnancy tests). Typically such assays are based on specific binding reactions, and therefore use sensitive reagents such as antibodies. A typical test device will comprise a strip of porous material within a plastics casing. The reagents are contained within the device in the dry state, and when sample liquid (such as urine) is applied to the device it migrates through the porous material and initiates one or more specific binding reactions which lead to the test result. Examples of such devices are described in EP-A-291194 the disclosures of which are included herein by reference.

These assay devices are manufactured and distributed on a large scale, and need to have a lengthy shelf life. The user expects the assay to be highly sensitive and therefore any deterioration in the performance of the assay reagents during storage would be unacceptable. To this end it is common practice for such devices to be provided in individual moisture-impervious packaging such as an aluminium foil pouch. A desiccant is provided within the pouch together with the assay device. Conventionally this is in the form of a small sachet of silica gel. As an alternative, a compressed tablet of desiccant (usually molecular sieve material) can be incorporated within the device itself. Both of these approaches have significant disadvantages.

The necessity to include a sachet of desiccant inside each foil pouch complicates the packaging process. More important, the sachet of desiccant is of no value to the consumer and must be discarded with the rest of the packaging. It can easily become separated from the remainder of the packaging. If mislaid in the home it may be found by an inquisitive child and perhaps ingested with potentially disastrous consequences.

The inclusion of a tablet of desiccant within the device itself adds a further step to the assembly process, and necessitates moulding features to accommodate and retain the tablet. In terms of storage stability there does not appear to be any extra benefit associated with having an internal tablet of desiccant compared to the effectiveness of an external sachet.

GENERAL DESCRIPTION OF THE INVENTION

By the invention we have found that all of these disadvantages can be overcome by incorporating desiccant within the material structure of one or more plastics mouldings from which the device is assembled.

The invention provides an assay device comprising a casing enclosing one or more reagents which are susceptible to moisture-induced degradation during storage, wherein the casing is constructed at least in part of desiccant-containing plastics material. Preferably the desiccant-containing plastics material is enrobed or shielded within non-desiccant-containing plastics material; this can be achieved, for example by sandwich injection moulding.

Conveniently, the desiccant-containing plastics material forms at least part of a removable cap or shroud which forms part of the device as supplied to the user; for example, the cap or shroud can protect means whereby sample liquid can be received into the remainder of the device.

A preferred embodiment of the invention is an assay device comprising within a casing an assay strip together with at least one reagent in the dry state which can participate in a specific binding reaction to reveal the assay result following application of a sample liquid to the device, the casing having means whereby the sample liquid can be applied directly or indirectly to the strip, and wherein a removable cap or shroud is provided to protect the sample liquid application means, the cap or shroud incorporating desiccant in an amount sufficient to enhance storage stability of the reagent. Preferably the cap or shroud is moulded of desiccant-containing plastics material.

Preferably the desiccant-containing plastics material comprises a blend of polystyrene and silica gel. This can be enrobed within conventional plastics material, such as polystyrene. Hence the cap or shroud is preferably manufactured by a process involving sandwich injection moulding.

Very suitable desiccant-containing plastics materials are described in EP-A-599690 the disclosures of which are incorporated herein by reference. A typical desiccant-containing plastics material will comprise, by weight, about 60–65% of thermoplastic or thermosetting polymer such as polystyrene and about 30% of powdered desiccant such as silica gel dust and/or molecular sieve dust. The properties of this blend can be improved by incorporating a few percent of elastomer, and minor amounts of fibrous material. Despite the presence of the desiccant, the blended material can be moulded and processed using the techniques commonly employed in the plastics moulding industry.

According to EP-A-599 690, an ideal desiccant-containing plastics material comprises a blend of:

any thermoplastic or thermosetting polymer, especially polystyrenes, polyolefins (polyethylene, polypropylene), polyamides, polyvinyl chloride alone or combined, or unsaturated polyesters, phenolic resins, bakelites and polyurethanes, alone or combined;

a desiccant such as silica gel and molecular sieves;

an elastomer, such as styrene-butadiene rubbers (SBR), styrene-ethylene-butadiene-styrene copolymers (SEBS), butyl rubbers, ethylene-propylene rubbers (EPR), ethylene-propylene-diene rubbers (EPDM), copolymers of ethylene-vinyl acetate (EVA), ethylene-acrylate or acrylonitrile-butadiene, polynorbornenes, polyisoprenes, polychloroprenes or polybutadienes;

and fibres of length between 0.5 and 4 mm, for example acrylic, polyester or polyamide fibres or natural fibres of animal origin such as wool or silk or of vegetable origin such as cotton or linen.

Optionally, the dessicant-containing plastics material may optionally also contain any conventional inorganic or organic additives, in particular plasticisers, stabilisers, dyes and pigments.

If desired, the desiccant-containing plastics material can be used to form any part of, or indeed the whole of, the plastics mouldings from which the assay device is prepared. However we have found that an ideal circumstance in which to use the desiccant-containing plastics material is in the manufacture of a separate cap or shroud associated with the assay device.

The assay device must have some means whereby sample liquid is applied to the device to initiate the assay. In some devices this is an orifice in the moulding, into which sample liquid can be added eg. dropwise using a pipette. In other devices the sample application is achieved by direct contact of the device with a sample source such as a urine stream. To facilitate sample collection in this latter situation, the device is sometimes provided with a protruding porous member which can take up sample liquid and transfer it elsewhere within the device. In all of these formats it is useful to have a removable cap or cover which can protect the site of sample addition.

There are a number of advantages associated with including the desiccant in the cap as distinct from any other part of the device moulding. The cap will usually be a relatively simple structure, whereas the main device mouldings may be of complex shape necessary to locate and retain specific physical components within the device. Difficulties may arise in attempting to mould a complex high-precision structure from the desiccant-containing plastics material. Moulding difficulties are much less likely to arise in the manufacture of the structurally simpler cap.

The cap will be a comparatively small part of the entire device, so less desiccant-containing plastics material will be required in the moulding. This may be important from cost considerations.

The presence of the desiccant within the plastics composition can cause the moulding to appear discoloured. For aesthetic reasons, pure white plastics mouldings are preferred for this type of device. The presence of the desiccant can be disguised by adding a pigment to the plastics composition. A device in which only the cap is coloured is more acceptable.

As a preferred embodiment of the invention, the moulding of the device which incorporates the desiccant-containing plastics material is preferably made of a sandwich structure wherein at least the exterior surfaces of the moulding are formed from non-desiccant-containing plastics material. An ideal combination is desiccant-containing polystyrene within a sheath of "pure" polystyrene. The exterior of the moulding therefore appears pure white but the presence of the desiccant in the interior of the moulding confers the required storage stability.

By incorporating the desiccant in the cap of the device, the assay device itself can be made smaller because no space is required within the device body to accommodate a desiccant tablet. Neither is there any necessity to leave room within the packaging to accommodate a desiccant sachet.

During assembly and packaging of a device containing sensitive reagents it is necessary that the device be sealed inside a dry environment as soon as possible. For this reason the desiccant should be capable of absorbing any atmospheric moisture in the immediate vicinity of the sensitive reagents as quickly as possible. In this respect both an external desiccant sachet and an internal desiccant tablet are very efficient. There is ready contact between the desiccant material and the atmosphere within and around the device. However, with the desiccant material entrapped within the plastics material it would be expected that the necessary rapid absorption of atmospheric moisture might be impaired. However we have found in comparative storage trials that the efficiency of the desiccant is not significantly impaired by its incorporation within the plastics moulding material. This is true even when the desiccant is contained only within the cap of the device. In this configuration the desiccant may be distant from the sensitive reagents. Even when the desiccant-containing plastic in the cap is totally enrobed within non-desiccant-containing plastics material, the effectiveness of the moisture-absorbing properties are not impaired. In practice, atmospheric moisture can pass through normal plastics materials, such as polystyrene of the type conventionally used in assay device mouldings. Hence by incorporating the desiccant within the cap of the device all of the storage benefits associated with the conventional desiccant systems are retained and the disadvantages of those systems are avoided. Optionally, the cap may be associated with the remainder of the device during storage by being present loose with the device in a common sealed pouch, or received on a portion of the device other than the sample-receiving means while in a sealed pouch, the cap only being applied to the sample-receiving means during usage of the assay device.

By way of example only, effective storage stability in an assay device can be achieved if the component of the device moulded from the desiccant-containing plastics material comprises a blend of about 1:1 desiccant-containing/non-desiccant containing material. Hence, for example, if a cap or cover for the device has a mass of about 1 gm, it can conveniently be made by sandwich injection moulding using about 0.5 gm of conventional polystyrene and about 0.5 gm of desiccant-containing polystyrene. An optimum level of desiccant is about 30% by weight of the desiccant-containing polystyrene. Hence the cap or cover can usefully comprise about 0.1–0.2 gm of desiccant, such as silica. In a typical "test stick" type of assay device, the cap comprises about 20–30% of the total mass of the plastics mouldings.

BRIEF DESCRIPTION OF THE DRAWINGS

By way of example only, a typical assay device of the invention incorporating a desiccant within the cap moulding material is now described with reference to the accompanying drawings, of which:

FIG. 1 represents an isometric view of an assay device with cap in accordance with the invention;

FIG. 2 represents a cross-sectional side elevation of the device and cap shown in FIG. 1.

DETAILED DESCRIPTION OF AN EMBODIMENT OF THE INVENTION

Figure 3:
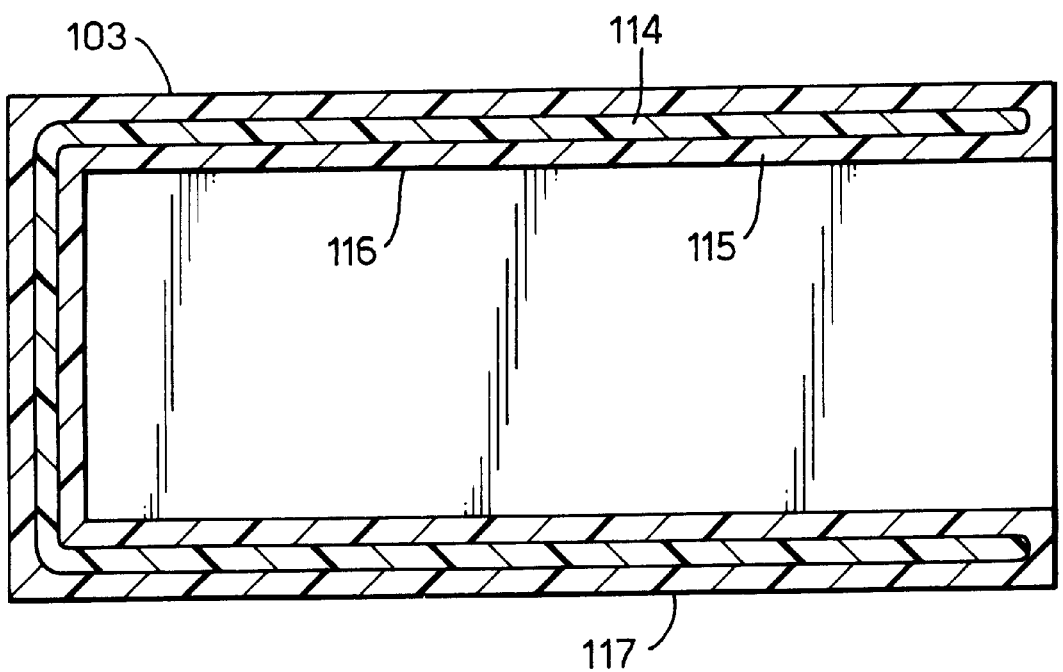
FIG. 3 shows the cross-sectional side elevation of the cap (as seen in FIG. 2) on a larger scale.

Referring to FIG. 1, the device comprises a housing 100 of elongate rectangular form having at one end 101 a portion 102 of reduced cross-sectional area. A cap 103 can be fitted onto portion 102 and can abut against the shoulder 104 at end 101 of the housing. Cap 103 is shown separated from housing 100. Extending beyond end 105 of portion 102 is a porous member 106. When cap 103 is fitted onto portion 102 of the housing, it covers porous member 106. Upper face 107 of housing 100 incorporates two apertures 108 and 109.

Referring to FIG. 2, it can be seen that housing 100 is of hollow construction. Porous member 106 extends into housing 100 and contacts a strip of porous carrier material 110, for example nitrocellulose. Porous member 106 and strip 110 overlap to ensure that there is adequate contact between these two materials and that a liquid sample applied to member 106 can permeate member 106 and progress into strip 110. Strip 110 extends further into housing 100. Strip 110 is "backed" by a supporting strip 111 formed of transparent moisture-impermeable plastics material. Strip 110 extends beyond apertures 108 and 109. Means are provided within housing 100 by webs 112 and 113 to hold strip 110 firmly in place. In this respect, the internal constructional details of the housing are not a significant aspect of the invention as long as the strip is held firmly in place within the housing, and porous member 106 is firmly retained in the housing and adequate fluid permeable contact is maintained between member 106 and strip 110. The transparent backing strip 111 lies between strip 110 and apertures 108 and 109 and can act as a seal against ingress of moisture from outside the housing 100 via these apertures. If desired, the residual space 114 within the housing can contain a moisture-absorbent sink to take up excess sample liquid from strip 110. Strip 110 will contain dry reagents (not shown), for example a first zone containing a labelled reagent which is mobile when the strip is moistened may lie in the region between the porous member 106 and aperture 108. Alternatively, a mobile labelled reagent can be located in the dry state in sample receiver 106, or in an intermediate porous pad (not shown). A second zone containing an immobilised unlabelled reagent will lie in the region exposed through aperture 108 in order that when the device has been used in an assay, the result can be observed through aperture 108. Aperture 109 provides means through which a control zone containing further reagents which may enable the adequate permeation of moisture through the strip to be observed.

FIG. 2 also shows the cap in cross section and its construction can be seen. Reference should also be made to FIG. 3 which gives the identical view of the cap on a much larger scale. The cap has been constructed by a mono-sandwich injection moulding process and the entire cap wall structure comprises a core 114 of desiccant-containing plastics material totally enrobed in an outer sheath 115 of non-desiccant-containing plastics material. Thus the entire visible surface of the cap which includes the inner surface 116 and the exterior 117 is formed of the non-desiccant containing material. No part of the desiccant-containing core is exposed to the atmosphere directly. This ensures that all visible surfaces of the cap comprise "pure" plastics material and the cap as a whole is aesthetically pleasing. Other constructions are possible. If desired, the entire cap can be moulded of the desiccant-containing plastics material. Alternatively the "pure" sheath may extend simply over the exterior of the cap, leaving the desiccant-containing material exposed on inner surfaces of the cap. One or more of the body mouldings that make up the device casing can also be made of dessicant-containing plastics material if desired.

In operation, the protective cap 103 is removed from the holder and member 106 is exposed to a liquid sample e.g. by being placed in a urine stream in the case of a pregnancy test. After exposing member 106 to the liquid sample for a time sufficient to ensure that member 106 is saturated with the sample, the cap 103 can be replaced and the device placed aside by the user for an appropriate period of time (e.g. two or three minutes) while the sample permeates test strip 110 to provide the analytical result. After the appropriate time, the user can observe the test strip through apertures 108 and 109 and can ascertain whether the assay has been completed by observing the control zone through aperture 109, and can ascertain the result of the assay by observing the second zone through aperture 108. Alternatively the assay device can be read by machine, with the assay result determined optically for example by reflectance or transmission through the strip (in which event one or more additional apertures may be required in the device casing.

During manufacture, the device can be readily assembled from, for example, plastics material with the housing 100 being moulded in two parts (an upper and lower half) which can be securely fastened together (e.g. by ultrasonic welding) after the porous member and test strip have been placed within one of the halves and then sandwiched between the two halves. The act of forming this sandwich construction can be used to "crimp" the porous member and test strip together to promote adequate liquid-conductive contact between them. Cap 103 is moulded as a separate complete item, by mono sandwich injection moulding so that the desiccant-containing plastics material is enrobed in the non-dessicant containing plastics material, as shown. If desired, apertures 108 and 109 can be provided with transparent inserts or covers which may ensure greater security against ingress of extraneous moisture from outside the housing.

The invention can be applied in the manufacture of any assay device which utilises sensitive assay reagents such as antibodies within a plastics casing. The nature of the sample liquid and the analyte or analytes being assayed is not critical. The invention therefore finds utility in a very wide range of test devices, which may be directed to the detection of urinary analytes such as hormones and their metabolites, for example human chorionic gonadotropin (hCG), luteinising hormone (LH), follicle stimulating hormone (FSH), estrone-3-glucuronide (E3G) and pregnanediol-3-glucuronide (P3G); analytes associated with sexually transmitted diseases, such as Chlamydia; drugs of abuse; and pathogenic organisms such as food pathogens, for example Listeria and Salmonella. The sample liquids involved can be body fluids such as urine, serum and whole blood; effluent samples, cultured blood samples; and foodstuff samples which have been subjected to microbial enrichment procedures.

EXAMPLE

The following example demonstrates that a desiccant-containing plastics material can be used in accordance with the invention to impart effective storage stability on an assay device. In this instance the test wss for urinary luteinising hormone (LH), and the test device was based on a sandwich immunoassay format conducted on a porous nitrocellulose strip within a polystyrene casing, using a mobile particle-labelled (blue-coloured latex) monoclonal antibody specific against LH, and an immobilised anti-LH monoclonal antibody in a detection zone on the strip. The test was conducted by dipping each device in standard LH-containing urine, and evaluated the assay result after 5 minutes. The relative accumulation of coloured latex in the detection zone was proportional to the urinary LH concentration. The result was determined in arbitrary units by optical transmission using red light, extinction of light transmission being assessed by comparison with a portion of the strip adjacent the detection zone. The test device was constructed in a manner comparable to that shown in FIGS. 1 to 3 and described above, except that the lower half of the casing also incorporated an aperture directly opposite to aperture 108 to permit light transmission through the strip. This second aperture was also sealed against gross ingress of extraneous moisture during sample collection. Each device had a cap by made by mono sandwich injection moulding, of construction as seen in FIG. 3. The core of the cap was made from a silica-containing polystyrene (blend containing about 30% silica and about 60% polystyrene) as broadly described in EP-A-599690, and the remainder of the cap comprised conventional white polystyrene. The core represented approximately 50% of the total material of the cap.

Devices of this type were packed under ambient conditions of temperature and humidity in conventional individual sealed aluminium foil pouches, and stored under controlled temperature conditions at ambient humidity, and sample devices used in LH tests periodically. As a comparison, identical devices (with caps moulded entirely from normal polystyrene) were stored under identical conditions, with each device provided with a conventional silica gel sachet in its foil pouch.

Tables I to III below give the comparative storage stability, expressed in terms of the LH assay results. No significant difference is seen, therefore confirming that the dessicant in the cap is just as effective as the conventional external sachet of dessicant.

TABLE I

STORAGE AT 21° C.

|  | EXTERNAL SILICA | SILICA IN CAP |
|---|---|---|
| 10 mIU/ml | 8.56 | 7.58 |
| 15 mIU/ml | 10.82 | 10.03 |
| 25 mIU/ml | 15.76 | 15.12 |
| 35 mIU/ml | 19.91 | 19.37 |
| 60 mIU/ml | 25.23 | 23.57 |

TABLE II

STORAGE AT 32° C.

|  | EXTERNAL SILICA | SILICA IN CAP |
|---|---|---|
| 10 mIU/ml | 7.93 | 7.02 |
| 15 mIU/ml | 11.45 | 10.20 |
| 25 mIU/ml | 16.47 | 15.83 |
| 35 mIU/ml | 17.58 | 20.51 |
| 60 mIU/ml | 25.27 | 23.91 |

TABLE III

STORAGE AT 40° C.

|  | EXTERNAL SILICA | SILICA IN CAP |
|---|---|---|
| 10 mIU/ml | 7.91 | 9.60 |
| 15 mIU/ml | 11.21 | 11.92 |
| 25 mIU/ml | 14.62 | 16.89 |
| 35 mIU/ml | 18.16 | 22.25 |
| 60 mIU/ml | 25.53 | 26.97 |

The effectiveness of the assay depends on both of the monoclonal antibody reagents, which are present in the device in the dry state, retaining a high level of biological activity despite prolonged storage.

What is claimed is:

1. An assay device packaged within a sealed moisture-impervious wrapping, said assay device consisting essentially of:

a) a casing;

b) an assay strip within said casing together with at least one reagent in the dry state which can participate in a specific binding reaction to reveal an assay result following application of a sample liquid to said device, said casing having means whereby the sample liquid can be applied directly or indirectly to said strip; and c) a removable cap or shroud to protect said sample liquid application means, said cap or shroud comprising a molded desiccant-containing plastics material incorporating desiccant in an amount sufficient to enhance storage stability of said reagent.

2. A device according to claim 1, wherein said desiccant-containing plastics material is enrobed or shielded within non-desiccant-containing plastics material.

3. A device according to claim 1, wherein said desiccant-containing plastics material comprises a blend of polystyrene and silica gel, and said enrobing plastics material comprises polystyrene.

4. A device according to claim 1, wherein said cap or shroud is manufactured by a process involving sandwich injection moulding.

5. A device according to claim 1, wherein said dessicant-containing plastics material consists essentially of a mouldable blend of:

a) about 60 to 65% by weight of a thermoplastic or thermosetting polymer; and b) about 30% by weight of powdered dessicant;

the remainder of said dessicant-containing plastics material comprising one or more minor components selected from the group consisting of elastomers, fibrous materials, plasticisers, stabilisers, dyes and pigments.

* * * * *